United States Patent
Schaefer et al.

(10) Patent No.: US 6,630,149 B1
(45) Date of Patent: Oct. 7, 2003

(54) BLISTER CONTAINING A TRANSDERMAL THERAPEUTIC SYSTEM AND A SINGLE DOSE FORM OF ADMINISTRATION

(75) Inventors: Wolfgang Schaefer, St. Augustin (DE); Hanshermann Franke, Neuwied (DE); Bodo Asmussen, Bendorf-Sayn (DE)

(73) Assignee: LTS Lohmann Therapie Systeme AG, Andernach (DE)

( * ) Notice: Subject to any disclaimer, the term of this patent is extended or adjusted under 35 U.S.C. 154(b) by 0 days.

(21) Appl. No.: 09/743,540

(22) PCT Filed: Jul. 2, 1999

(86) PCT No.: PCT/EP99/04614

§ 371 (c)(1),
(2), (4) Date: Mar. 23, 2001

(87) PCT Pub. No.: WO00/02538

PCT Pub. Date: Jan. 20, 2000

(30) Foreign Application Priority Data

Jul. 11, 1998 (DE) .......................................... 198 31 263

(51) Int. Cl.⁷ ................................................. A61K 9/70
(52) U.S. Cl. ....................... 424/400; 424/451; 424/464; 424/449; 424/489

(58) Field of Search .......................... 424/45, 400, 451, 424/464, 489, 449

(56) References Cited

U.S. PATENT DOCUMENTS

| 4,736,849 A | | 4/1988 | Leonard et al. |
| 5,108,995 A | * | 4/1992 | Casper ........................ 514/170 |
| 5,686,112 A | * | 11/1997 | Liedtke ....................... 424/489 |
| 5,855,905 A | | 1/1999 | Oettel et al. |

FOREIGN PATENT DOCUMENTS

| DE | 297 19 070 | | 10/1997 |
| EP | 0307352 B1 | * | 7/1988 |
| EP | 0307352 | | 3/1989 |
| WO | WO 9109731 | | 7/1991 |
| WO | WO 9901132 | | 1/1999 |

* cited by examiner

Primary Examiner—Thurman K. Page
Assistant Examiner—Rachel M. Bennett
(74) Attorney, Agent, or Firm—Jordan and Hamburg LLP

(57) ABSTRACT

A form of administration for medical active agents in the form of a blister is characterized in that it contains a transdermal therapeutic system and at least one single dose form of the active agent next to each other.

10 Claims, 1 Drawing Sheet

Figure 1:
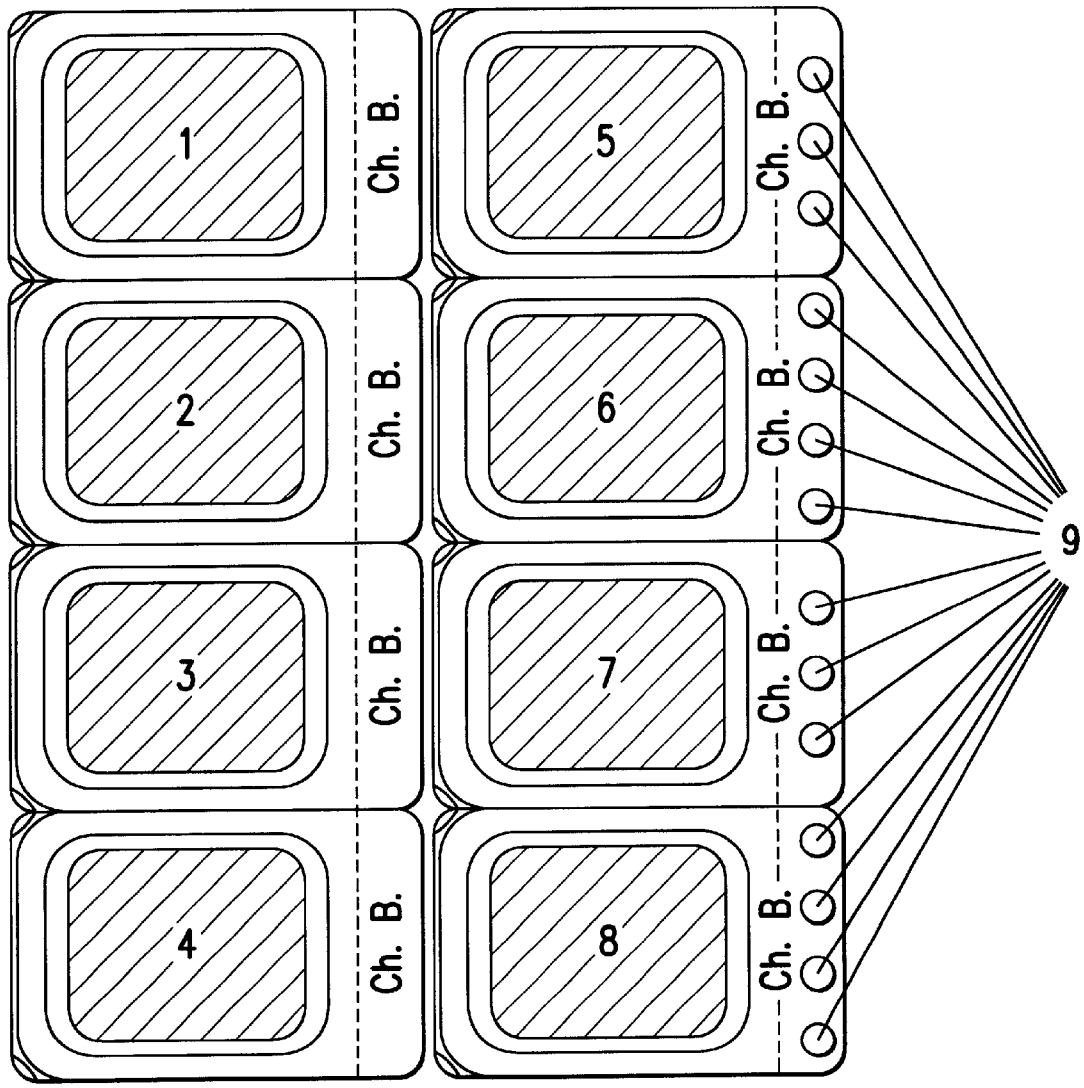

BLISTER CONTAINING A TRANSDERMAL THERAPEUTIC SYSTEM AND A SINGLE DOSE FORM OF ADMINISTRATION

This application a 371 of PCT/EP99/04614 filed Jul. 2, 1999.

The invention relates to a dosage form for medicinal active ingredients in blister form, which makes it possible to administer simultaneously a transdermal therapeutic system (TTS) and at least one single-dose active ingredient.

It is customary in hormone replacement therapy to combine administration of the basic hormone with administration of another hormone in order to avoid side effects. This applies, for example, to oestradiol administration, which takes place with administration of a gestagen. Since long-term, continuous administration of the basic hormone is desired, a suitable administration form has proved to be the transdermal therapeutic system (TTS), with which the active ingredient is delivered to the skin in controlled manner via a defined contact area of an active ingredient reservoir. The system preferably comprises a pressure-sensitive adhesive. If discontinuous concomitant medication with another hormone is desired, this usually takes place in tablet form. The tablets are normally stored separately and can be manipulated in accordance with the administration schedule only with difficulty. This type of dosage forms is thus extremely unfavourable for patient compliance.

It was therefore an object of the invention, for compliance reasons, to create a suitable packaging procedure for simultaneous administration of medicinal active ingredients via the transdermal and non-transdermal route. This was intended to ensure that the patient is aided, by an appropriate design of packaging, in implementing where possible intake of single doses at defined times.

The achievement of the object has now been found in a blister form which, besides the TTS, contains at least one single-dose active ingredient form. The TTS is packed individually in a blister but may also be fixed to the dosage form in another way, such as, for example, by means of the pressure-sensitive adhesive contact area. Accommodation in a blister is also the method of choice for the single-dose active ingredient form, which is preferably a tablet, it also being possible, of course, to conceive other attachment mechanisms.

Joining together several blister forms has proved advantageous for longer-term administration. This means for the patient that his administration regimen is fixed accurately and unambiguously for weeks. The series of blister forms may perfectly well include those which have no single-dose active ingredient form, if required for therapeutic reasons.

The single-dose active ingredient form is usually designed for non-transdermal administration. Otherwise, care must be taken that bolus-like release is ensured. Besides or in place of systemic active ingredients it is possible for the single-dose active ingredient form also to contain preparations for topical pretreatment and/or after-treatment of the TTS administration area. These preparations may, for example, improve the skin permeability of the active ingredient from the TTS or prevent or even reverse harmful skin changes after administration of the TTS. Last but not least, the single-dose active ingredient form may also contain one or more TTS active ingredients in order to cover the TTS lag time or generate an additional plasma peak required by the circadian rhythm.

The following example, illustrated by FIG. 1, summarizes the compliance-ensuring aspects of the novel dosage form with the aid of a unit composed of eight TTS 1 to 8, which is provided for a treatment period of 28 days. 9 indicates the single-dose active ingredient forms, none of which are contained in 1–4.

The following table reflects the course of administration for an oestrogen/gestagen treatment:

|  | No. of the blister form | Duration of wearing the blister form |
|---|---|---|
| Oes treatment without gestagen administration | Blister No. 1 | 1st, 2nd, 3rd day |
|  | Blister No. 2 | 4th, 5th, 6th, 7th day |
|  | Blister No. 3 | 8th, 9th, 10th day |
|  | Blister No. 4 | 11th, 12th, 13th, 14th day |
| Oes treatment in combination with gestagen administration in tablet form | Blister No. 5 | 15th, 16th, 17th day |
|  | Blister No. 6 | 18th, 19th, 20th, 21st day |
|  | Blister No. 7 | 22nd, 23rd, 24th day |
|  | Blister No, 8 | 25th, 26th, 27th, 28th day |

A gestagen-free treatment period of 14 days is followed by provision of a gestagen administration for each day of the TTS administration (alternating three and four days) in the last two weeks.

As the example illustrates, the invention provides a reliable means for permanently improving the compliance of patients on TTS administration with an additional single-dose active ingredient form.

The compliance can be increased by joining several blister forms together or labelling the individual blisters in the required sequence of use.

What is claimed is:

1. Blister pack for pharmaceuticals, comprising at least one blister form, wherein said blister forms contains a single transdermal therapeutic system with which an active ingredient is delivered to the skin in controlled manner via a defined contact area of its active ingredient-containing reservoir and the blister form also contains at least one single-dose active ingredient for non-transdermal administration.

2. Blister pack according to claim 1, comprising a plurality of blister forms joined together to increase compliance.

3. Blister pack according to claim 1, in which the individual blister forms are labeled in the required sequence of use to increase compliance.

4. Blister pack according to claim 2 or 3, in which at least one of the blister forms contains no single-dose active ingredient forms.

5. Blister pack according to any one of claims 1 to 3, in which the single-dose active ingredient forms contain pharmaceutical preparations for topical treatment before and/or after the transdermal therapeutic system administration.

6. A blister pack for pharmaceuticals comprising an integral substrate having at least two receptacles formed thereon, a transdermal therapeutic system contained in a first of the receptacles and a single-dose pharmaceutical contained in a second of the receptacles, whereby a user of the blister pack is reminded that the user is to use the contents of the first and the second receptacles according to a preset regimen.

7. A blister pack according to claim 6, further comprising indicia adjacent the receptacles for additionally reminding the user of the blister pack of the preset regimen.

8. Blister pack according to claim 6 or 7, wherein the single-dose pharmaceutical is for non-transdermal administration.

9. Blister pack according to claim 6 or 7, wherein the single-dose pharmaceutical is for topical application before and/or after administration of the transdermal therapeutic system.

10. Blister pack according to claim 8, wherein the single-dose pharmaceutical contains at least one pharmaceutical also administered by the transdermal therapeutic system.

* * * * *